United States Patent [19]

Lewis et al.

[11] Patent Number: 5,456,884
[45] Date of Patent: Oct. 10, 1995

[54] CASSETTE AND CUVETTE LOADING MECHANISM

[75] Inventors: Gregory D. Lewis, Cary; Roger G. Roberts, Raleigh; Thomas B. Givens, Rougemont, all of N.C.

[73] Assignee: Akzo Nobel N.V., Arnhem, Netherlands

[21] Appl. No.: 261,129

[22] Filed: Jun. 14, 1994

Related U.S. Application Data

[62] Division of Ser. No. 916,712, Jul. 22, 1992, Pat. No. 5,364,592.
[51] Int. Cl.⁶ ................................................ G01N 21/13
[52] U.S. Cl. ........................ 422/66; 422/63; 422/99; 422/102; 422/104; 220/559; 221/154; 221/227; 221/232; 221/270; 221/279
[58] Field of Search ........................... 422/63, 104, 102, 422/103, 99, 66; 221/229, 154, 227, 232, 270, 279

[56] References Cited

U.S. PATENT DOCUMENTS

4,804,107  2/1989  Bergstedth .......................... 221/227
4,985,207  1/1991  Hayashi ............................. 422/102

Primary Examiner—James C. Housel
Assistant Examiner—Harold Y. Pyon
Attorney, Agent, or Firm—Gregory R. Muir

[57]  ABSTRACT

A mechanism is provided for loading the cassette into an operative relationship with a machine for dispensing contents of the cassette for use by the machine. The loading mechanism includes a base adapted for being fixedly mounted on the machine. The loading mechanism also includes a holder for releasably holding the cassette. The holder has one end pivotally connected to the base for pivoting about an axis for moving the cassette between a first position at which the holder releasably receives the cassette and a second position at which the cassette is placed in an operative relationship with the machine. The loading mechanism further includes a linkage mechanism coupled between the base and the holder for translating the holder along the axis as the holder is pivoted between the first and second positions.

9 Claims, 6 Drawing Sheets

CASSETTE AND CUVETTE LOADING MECHANISM

CROSS-REFERENCE TO RELATED APPLICATIONS

This is a division of application Ser. No. 07/916,712 filed Jul. 22, 1992, now U.S. Pat. No. 5,364,592.

This application relates to the subject matter of Ser. No. 07/833,950, filed Feb. 11, 1992, now U.S. Pat. No. 5,236,666 the subject matter of which is incorporated herein by reference.

BACKGROUND OF THE INVENTION

1. Field of the Invention

This invention relates to the field of laboratory testing of fluid samples and, more particularly, to a means for quickly and effectively loading sample reaction chambers into an automated sample handling/testing device.

2. Description of the Related Art

In the field of laboratory testing of fluid samples, such as medical testing of blood and urine samples, hospitals and testing laboratories have largely turned to automated machines to perform routine chemistry testing on body fluids. Several factors have weighed very heavily in influencing this decision. First, testing of the fluid samples is often very repetitive in nature, yet it requires a high level of concentration to avoid errors which might lead to critical mistakes in treatment. Second, manual handling of fluid samples increases risk to the laboratory technician for contracting a communicable disease, e.g. AIDS, hepatitis etc. Third, automated sample handling and testing frees up the laboratory technician to carry out other less routine functions where human decision making skills can be uniquely utilized.

To obtain these and other advantages in laboratory testing of fluid samples, automated sample handling/testing machines have been employed. When properly calibrated and adequately maintained, these automated devices can efficiently perform repetitive testing procedures with great accuracy and precision.

Chemical analysis of the fluid sample by the automated sample handling/testing device often occurs in a reaction chamber called a cuvette. These transparent cuvettes are somewhat analogous to a test tube employed in manual testing. Typically, the automated sample handling/testing device dispenses a fluid sample into a cuvette along with one or more test specific reagents and diluents. After thorough mixing of the solution and a precisely timed delay, a photometric analysis can be employed to detect changes in the solution. The degree and/or rate of change can be equated to a numerical test result and compared to a normal range of test results as determined from healthy individuals.

One of the key concerns in automated testing of fluid samples is a device for storing and reliably dispensing cuvettes as needed to the automated sample handling/testing device. There is a need to provide a loading device and container for quickly and effectively loading an automated instrument with a supply of cuvettes to provide continuous processing of fluid samples so as to free the laboratory technician to perform other tasks in the lab.

SUMMARY OF THE INVENTION

It is an object of this invention to provide a cassette for storing and reliably dispensing cuvettes.

It is another object of this invention to provide means for loading the cassette into the sample handling/testing device from which the cuvettes can then be automatically dispensed for use by the handling/testing device.

The above and other objects of the invention are accomplished by provisions of a cassette for storing and dispensing cuvettes comprising: an enclosable frame defining an interior volume for storing cuvettes, including: a removable cover for securing a plurality of cuvettes loaded into the frame when the cover is removed, a side wall including a pivotally mounted door for pivoting between a closed position and an open position through which the cuvettes can be dispensed from the cassette, and a locking means for locking the door in the closed position to avoid an inadvertent dispensing of cuvettes.

The above and other objects of the invention are further accomplished by provision of a mechanism for loading a container into an operative relationship with a machine for dispensing contents of the container for use by the machine, comprising: a base adapted for being fixedly mounted on the machine; a holder for releasably holding the container, the holder having one end pivotally connected to the base for pivoting about an axis for moving the container between a first position at which the holder releasably receives the container and a second position at which the container is placed in an operative relationship with the machine; and linkage means coupled between the base and the holder for translating the holder along the axis as the holder is pivoted between the first and second positions.

The invention will be understood in greater detail with reference to the specific embodiment thereof that is illustrated in the drawings.

DETAILED DESCRIPTION OF THE PREFERRED EMBODIMENT

In describing the illustrated embodiment of the invention, corresponding parts in different figures are designated with the same reference numerals in order to minimize repetitive descriptions.

Figures 1, 2:
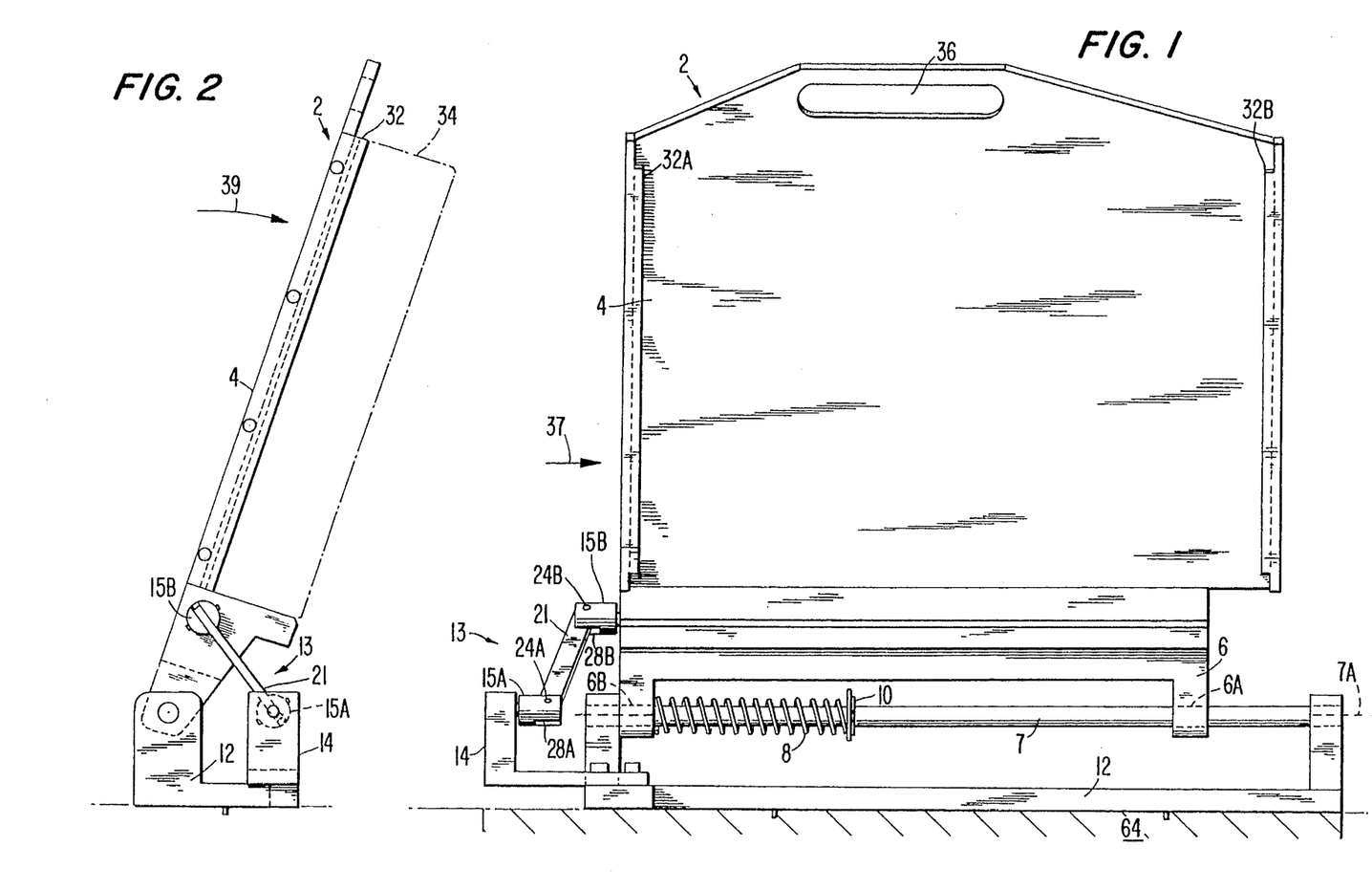
FIG. 1 is a front view of a mechanism for loading cassettes into an instrument in accordance with the present invention.
FIG. 2 is a side view of the mechanism shown in FIG. 1.

Referring now to the drawings, FIG. 1 illustrates a pivotable and translatable loading mechanism 2. A holder 4 is pivotally connected at one end 6 to a pivot rod 7 having a longitudinal axis 7A. Holder 4 has two bores 6A, 6B through which pivot rod 7 freely passes to allow pivoting of holder 4 about axis 7A. A compression spring 8 is inserted onto pivot rod 7 between bores 6A and 6B and held in place by rod nut 10. Rod 7 is held by a base 12 which is fastened to a machine 64. A dual action link 13 is connected between holder 4 and base 12 via a link support 14. A first rotatable member 15A is rotatably mounted at one end to support 14 and a second rotatable member 15B is rotatably mounted at one end to cover 4. The unmounted ends of members 15A and 15B contain respective slots 28A and 28B. A blade 21 is pivotally connected between slots 28A and 28B of the respective unmounted or free ends of members 15A and 15B by respective pins 24A and 24B. A respective holder guide 32A, 32B is found at opposing sides of the underside of holder 4 adjacent pivot end 6 for releasably holding a container, such as a cassette for dispensing cuvettes. A handle 36 is located opposite pivot end 6 of holder 4 to facilitate manual rotation of holder 4. During rotation of holder 4 about pivot rod 7 holder 4 will translate along pivot rod 7 in the direction shown by arrow 37.

FIG. 2 shows a side view of the loading mechanism 2 in a first or loading position. An enclosable cassette frame or container 34 (shown in dash-dot line) is in sliding engagement with holder guides 32A and 32B. A directional arrow 39 indicates the direction of rotation of the loading mechanism 2 from the loading position to a second position to place the cuvette in an operative position with a machine for (not shown) dispensing cuvettes.

Figure 3:
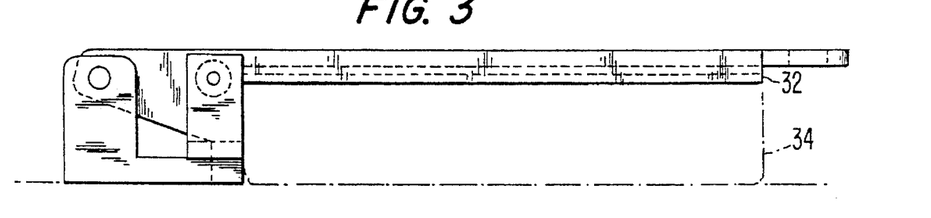
FIG. 3 is a side view of the mechanism of FIG. 1 and a cassette in an instrument in accordance with the present invention.

FIG. 3 shows the loading mechanism after it has been rotated and translated into a second position for dispensing the contents of container 34 into the machine (not shown).

Figure 4:
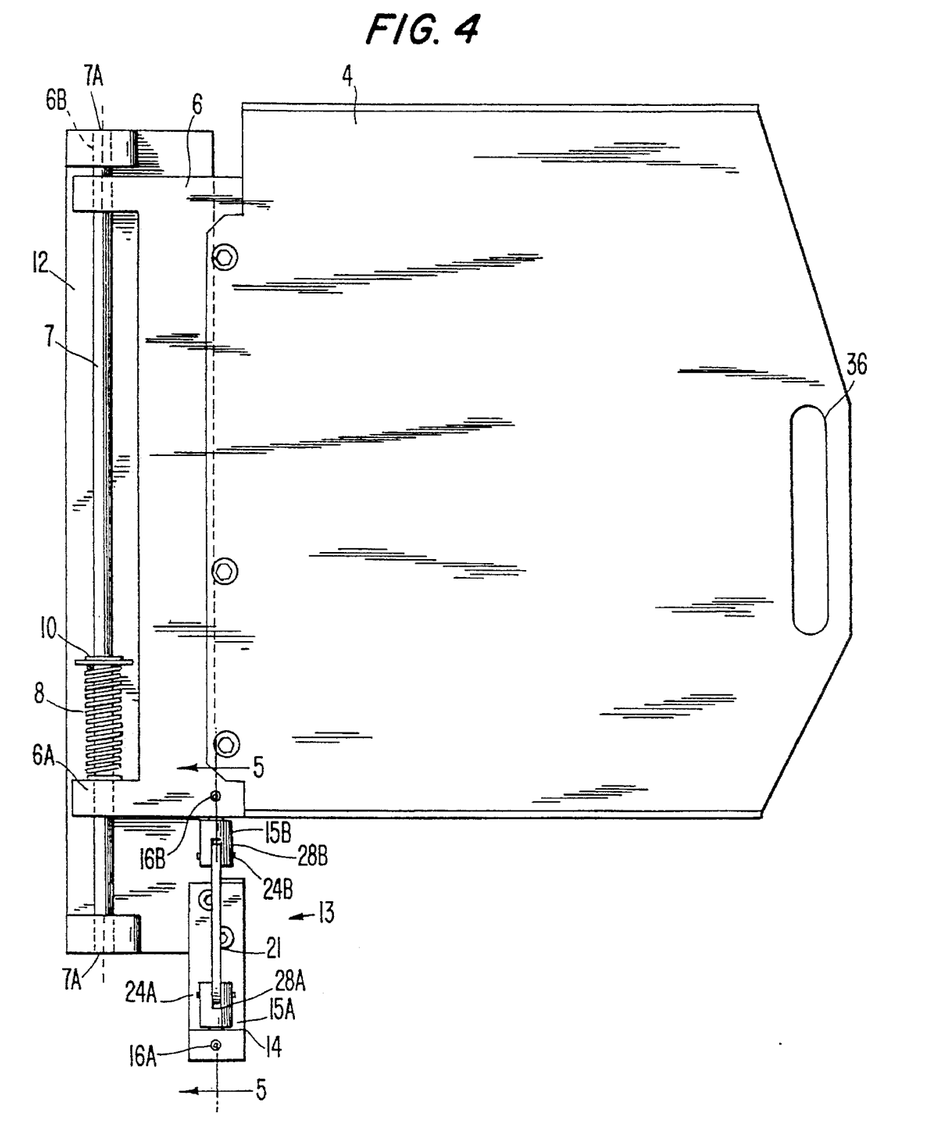
FIG. 4 is a top plan view of the mechanism as shown in FIG. 3.

FIG. 4 shows a top plan view of the loading mechanism in the second position as shown in FIG. 3. Set screws 16A and 16B are shown to fasten dual action link 13 to pivot end 6 and support 14, respectively. Dual action link 13 is located at a distance from pivot axis 7A such that blade 21 when fully extended is in a direction parallel to but offset from longitudinal pivot axis 7A. Since holder 4 is constrained to pivot about pivot axis 7A, blade 21 can only become fully extended by forcing holder 4 to translate along rod 7. Compression spring 8 is substantially compressed against fixed rod nut 10 due to the translation of holder 4 during pivoting of the holder into the second or closed position. Compression spring 8 provides a resistance to closing holder 4 and an aid to opening holder 4 as the spring is released.

Figure 5:
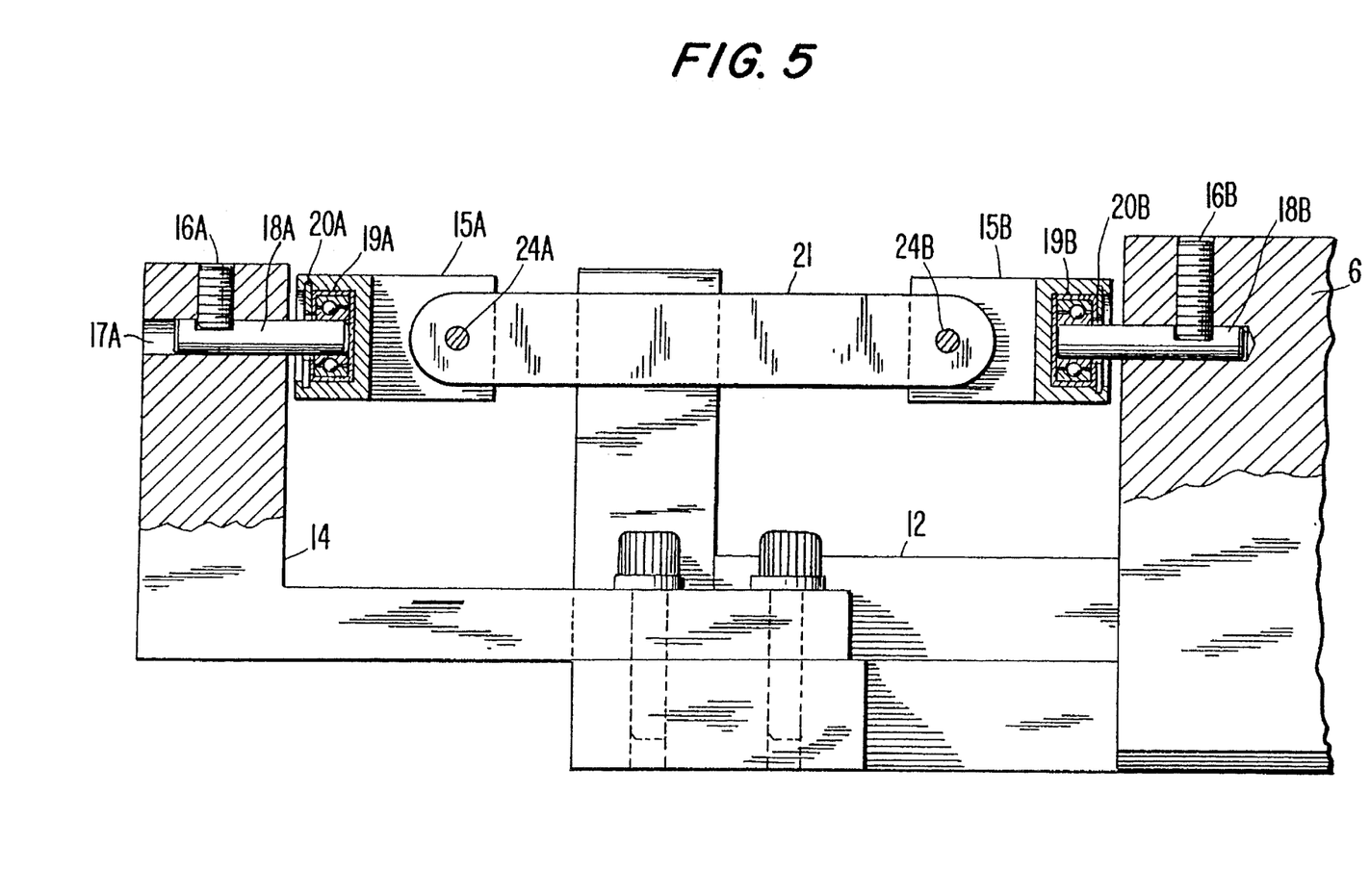
FIG. 5 is a sectional view taken along the line 5—5 of FIG. 4 of the mechanism in accordance with the present invention.

FIG. 5 illustrates a sectional view of dual action link 13. Posts 18A and 18B are shown to connect members 15A and 15B, respectively, to link support 14 and pivot end 6 of holder 4, respectively. Bearings 19A and 19B are employed for rotatably mounting members 15A and 15B, respectively, about posts 18A and 18B, respectively. Clamps 20A and 20B are employed to fix bearings 19A and 19B, respectively, inside the mounting ends of members 15A and 15B, respectively.

Figure 6:
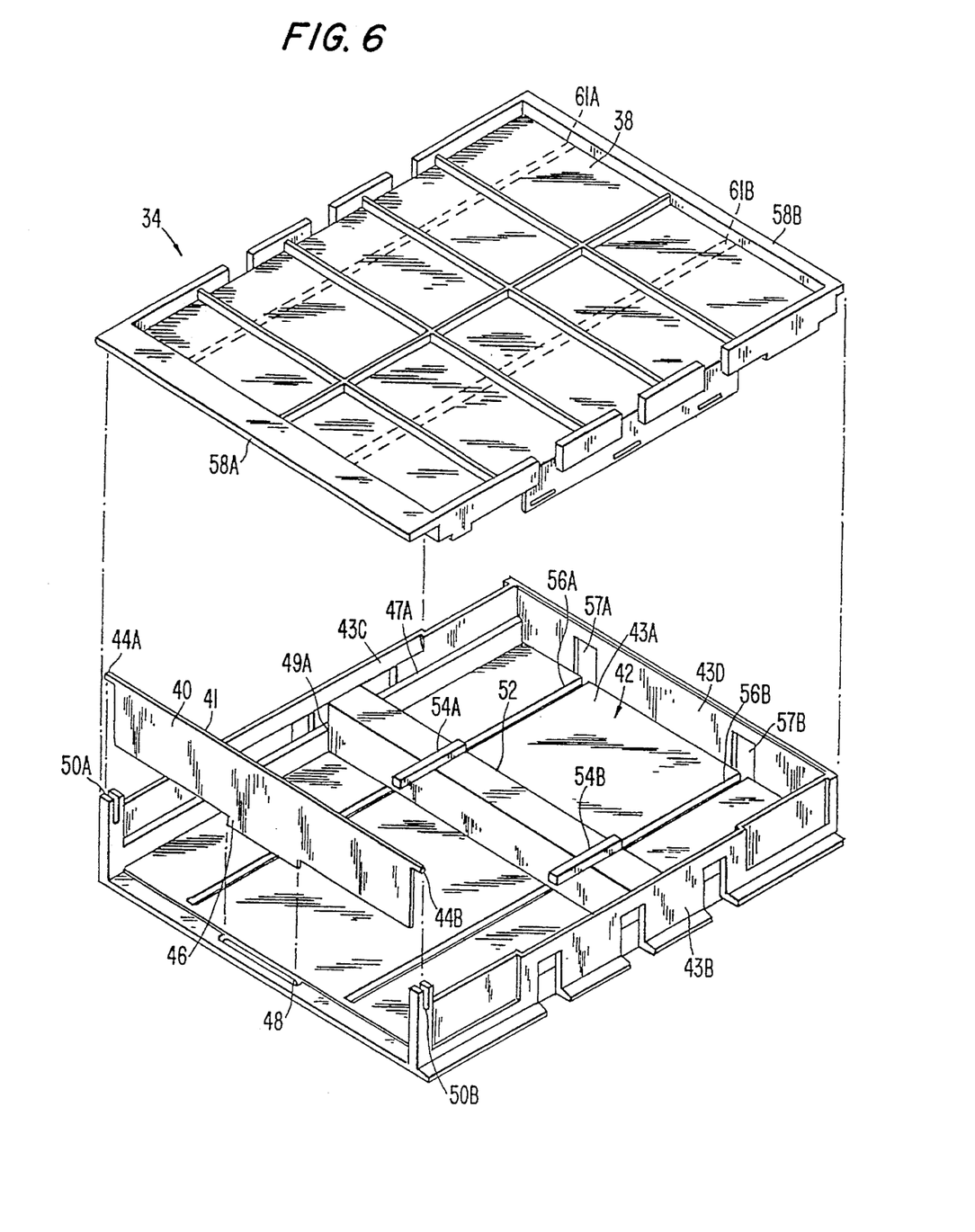
FIG. 6 is an exploded view of a cassette in accordance with the present invention.

FIG. 6 shows an exploded view of an enclosable cassette frame 34. A removable cover 38 and a door 40 are fastenable upon a cassette body 42 having a bottom 43A side walls 43B, 43C and a rear wall 43D. Door 40 has a top edge 41 which is extended beyond both ends of the doors to form pivot pins 44A and 44B. Pivot pins 44A and 44B are pivotally located in respective pivot grooves 50A and 50B. A locking tab 46 along the bottom edge of door 40 is locatable into a through slot 48 in cassette body 42. A guide bar 52 is slidably disposed in cassette body 42. Edge guides 49A and 49B are located at a respective side edge of guide bar 52 for sliding engagement along interior ridges 47A and 47B of side walls 43C and 43B, respectively. Guide rails 54A and 54B located atop guide bar 52 slide along parallel longitudinal cover grooves 61A and 61B, respectively, in the underside of cover 38. Cover 38 has respective cassette lips 58A and 58B for slidable engagement with guides 32A and 32B, respectively, of holder 4 (FIGS. 1–5) for releasably holding enclosable cassette frame 34. Cassette body 42 is provided with drive ports 57A and 57B in rear wall 43D and drive slots 56A and 56B through which a mechanism (not shown) passes to push guide bar 52 along cover grooves 61A and 61B so that the contents of enclosable cassette frame 34 are dispensable through door 40 as required by the machine (not shown).

Figure 7:
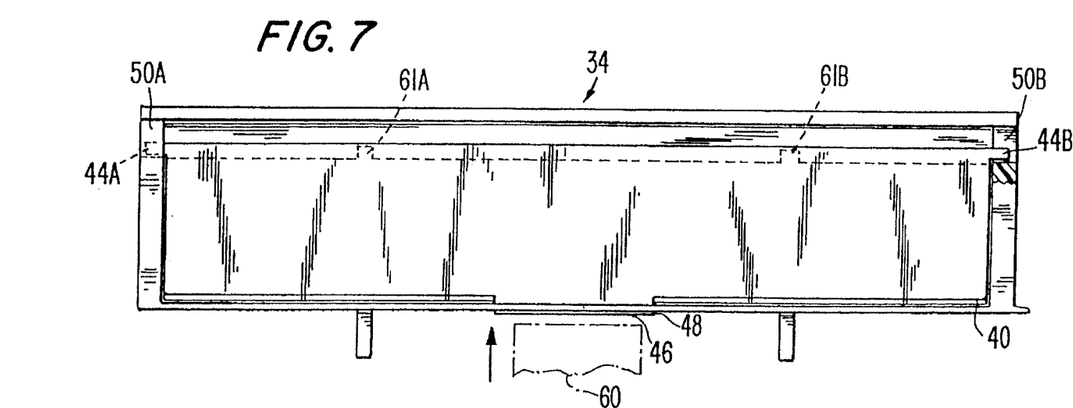
FIG. 7 is a front view of the cassette with the door in a locked position in accordance with the present invention.

FIG. 7 shows a tab release 60 in dash-dot line, which is part of the machine (not shown) into which cassette frame 34 is inserted, for disengaging locking tab 46 from through slot 48 so that door 40 can be opened. Door pivots 44A and 44B are shown in a second or locked position of pivot grooves 50A and 50B, respectively.

Figure 8:
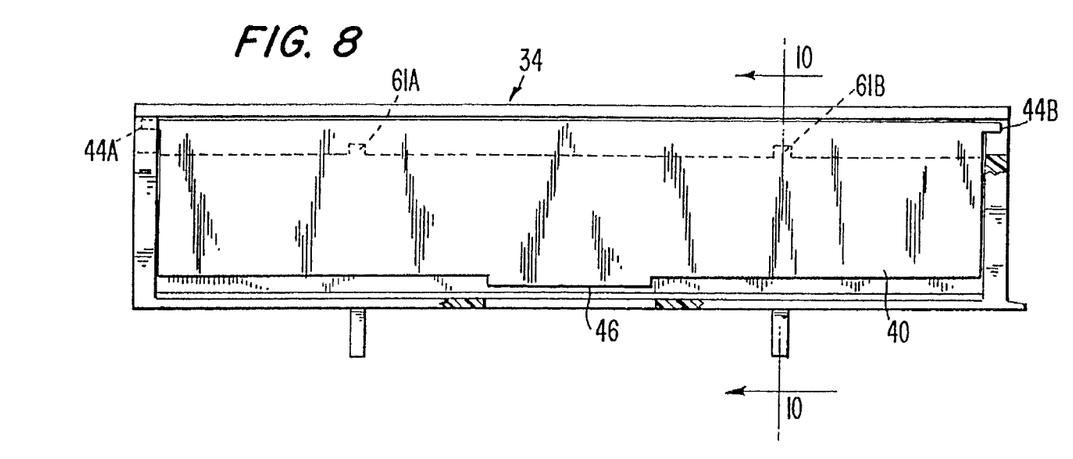
FIG. 8 is a front view of the cassette with the door in an unlocked position in accordance with the present invention.

FIG. 8 shows the effect of tab release 60 having forced locking tab 46 from through slot 48. Pivot pins 44A and 44B are in the up or unlocked position of pivot groove 50A and 50B, respectively.

Figure 9:
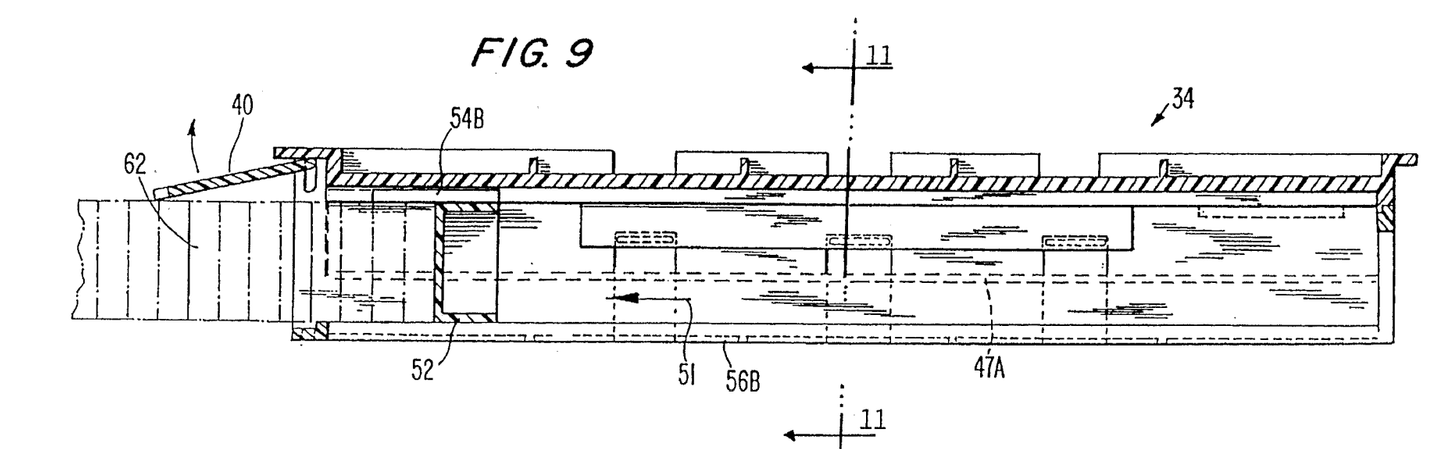
FIG. 9 is a sectional view taken along line 10—10 of FIG. 8 with cuvettes being dispensed in accordance with the present invention.

FIG. 9 shows a directional arrow 51 indicating the advancement of guide bar 52 for dispensing a column of cuvettes 62 shown in dash-dot line. Guide bar 52, under the influence of a drive mechanism (not shown), exerts pressure upon cuvettes 62 which open door 40 from its unlocked position shown in FIG. 8.

Figure 10:
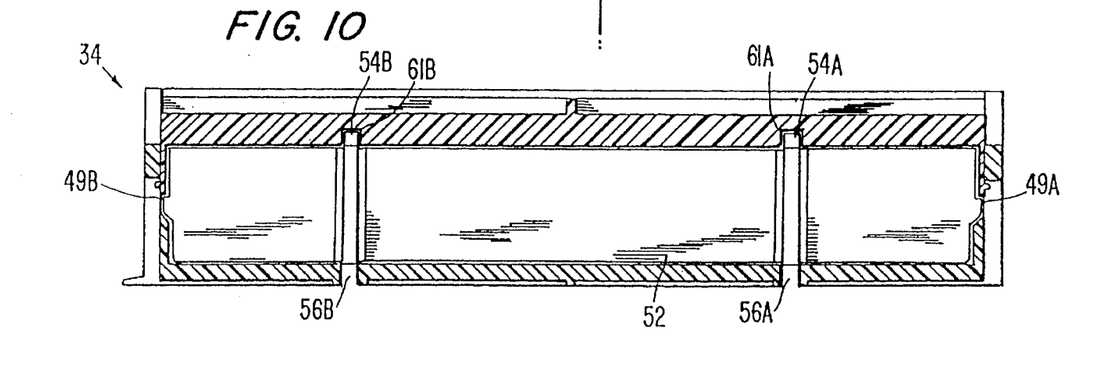
FIG. 10 is a sectional view taken along line 11—11 of FIG. 9 in accordance with the present invention.

FIG. 10 shows guide pins 54A and 54B in cover grooves 61A and 61B, respectively, indicating the parallel movement of guide bar 52 along longitudinal cover grooves of enclosable cassette frame 34. Uniform dispensing of the cuvettes of the enclosable cassette frame 34 machine is thus attained.

In operation, cuvettes 62 are placed into the interior volume of enclosable frame 34 in front of guide bar 52. Door 40 is inserted into position on cassette body 42 so that pivot pins 44A and 44B are located in pivot grooves 50A and 50B, respectively, and locking tab 46 is located in through slot 48. Removable cover 38 is then placed onto cassette body 42, covering pivot grooves 50A, 50B. Enclosable cassette frame 34 is next loaded onto loading mechanism 2 which is in the first or loading position (FIG. 1). Loading of cassette 34 is accomplished by slidably engaging cassette lips 58A and 58B along holder guides 32A and 32B, respectively. Following loading of the cassette, handle 36 is grasped to rotate holder 4 of loading mechanism 2 about pivot axis 7A. Upon rotation of holder 4 about longitudinal pivot axis 7A, dual action link 13 simultaneously applies a translational force to holder 4 in the pivot region. This translation forces pivot end of holder 4 against compression spring 8 located along pivot rod 7. As shown in FIG. 4, holder 4 has been pivoted into the closed position for dispensing cuvettes into a sample handling/testing machine (not shown in FIG. 4). Dual action link 13 is shown in its fully extended position and compression spring 8 has been substantially compressed against rod nut 10 during translation of holder 4 along pivot rod 7.

FIG. 7 schematically demonstrates a tab release 60 from machine 64 in motion to release locking tab 46 from through slot 48. Tab release 60 applies a sufficiently upward or vertical force to locking tab 46 to cause removable cover 38 to become slightly concave such that locking tab 46 clears through slot 48.

In FIG. 8, locking tab 46 has been forced out of through slot 48 and pivot pins 44A and 44B have been forced to a top region of pivot grooves 50A and 50B, respectively to unlock the door. The action of tab release 60 slightly concaves removable cover 38 near the region of the door to overcome the biasing of the door in the locked position. Machine 64 employs a driving mechanism, as indicated by arrow 51 in FIG. 9, through drive ports 57A and 57B to drive or push guide bar 52 against cuvettes 62 inside of enclosable cassette frame 34. This action will cause cuvettes 62 to press against door 40 thereby causing door 40 to pivot open about pivot pins 44A and 44B which are located above both the top of cuvettes 62 and guide bar 52. At this point pivot pins 44A and 44B return to a lower position in pivot grooves 50A and 50B, respectively. This action is illustrated in FIG. 9 where bar 52 acts uniformly to dispense a column of cuvettes 62 from enclosable cassette frame 34.

While there has been described what is presently believed to be the preferred embodiment of the invention, it will be apparent to one skilled in the art that numerous changes can be made in the structure set forth in the foregoing embodiment without departing from the invention as described herein and as defined in the appended claims.

What is claimed is:

1. A mechanism for loading a container into an operative relationship with a machine for dispensing contents of the container for use by the machine, comprising:

a base adapted for being fixedly mounted on a machine;

a holder having guide means for releasably holding a container, said holder having one end pivotally connected to said base for pivoting about an axis for moving the container between a first position and a second position, said guide means constructed so as to releasably hold the container at said first position and constructed such that when in said second position the container is placed in an operative relationship with the machine; and linkage means connecting said base and said holder for causing translational movement of said holder along the pivot axis as said holder is pivoted between the first and second positions.

2. A mechanism as recited in claim 1, wherein said holder includes at least one guide for releasably holding the container.

3. A mechanism as recited in claim 1, wherein said linkage means has one end connected to said holder at a point disposed radially away from said pivot axis, and wherein said linkage means has another end connected to said base at a position disposed both axially and radially away from where said holder one end is pivotally connected to said base.

4. A mechanism as recited in claim 1, wherein said pivot axis comprises a longitudinal rod and a compression spring fixable along said longitudinal rod, such that the translational movement of the holder along the axis between the first and second positions releasably compresses the spring.

5. A mechanism as recited in claim 4, wherein said holder includes a bore through said one end for pivoting about said pivot axis.

6. A mechanism as recited in claim 1, wherein said linkage means is located at a distance from said pivot axis.

7. A mechanism as recited in claim 6, wherein said linkage means includes a support attached to said base; first and second rotatable members each having a rotatably mountable end and a free end, said rotatably mountable end of said first member being mounted to said support and said rotatably mountable end of said second member being mounted to said holder; and a blade having first and second ends, said first and second blade ends being pivotally connected between respective free ends of said first and second members.

8. A mechanism as recited in claim 7, wherein said blade is parallel to and offset from the pivot axis when said holder is in said second position.

9. A mechanism as recited in claim 7, wherein said free ends each include a slot disposed for pivotally mounting said blade.

* * * * *

UNITED STATES PATENT AND TRADEMARK OFFICE
CERTIFICATE OF CORRECTION

PATENT NO.  : 5,456,884
DATED       : October 10, 1995
INVENTOR(S) : Gregory D. Lewis It is certified that error appears in the above-indentified patent and that said Letters Patent is hereby corrected as shown below:

Please correct the inventor's name on the title page by deleting "et al." in line 2, after "Lewis"; and in lines 5 - 7, first column, by deleting "Roger G. Roberts, Raleigh; Thomas B. Givens, Rougemount, all of".

Signed and Sealed this

Twelfth Day of March, 1996

Attest:

BRUCE LEHMAN

*Attesting Officer*     Commissioner of Patents and Trademarks